United States Patent
Gerlach et al.

(12) 
(10) Patent No.: US 6,552,186 B2
(45) Date of Patent: Apr. 22, 2003

(54) β-LACTAM PRODUCTION

(75) Inventors: Benjamin Gerlach, Breitenbach (AT); Johannes Ludescher, Breitenbach (AT); Klaus Totschnig, Kundl (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/975,436

(22) Filed: Oct. 11, 2001

(65) Prior Publication Data

US 2002/0128469 A1 Sep. 12, 2002

Related U.S. Application Data

(63) Continuation of application No. PCT/EP00/03428, filed on Apr. 14, 2000.

(30) Foreign Application Priority Data

| Apr. 15, 1999 | (AT) | ................................................ | 673/99 |
| Apr. 29, 1999 | (AT) | ................................................ | 763/99 |
| May 5, 1999 | (AT) | ................................................ | 800/99 |
| Jun. 14, 1999 | (AT) | ................................................ | 1042/99 |

(51) Int. Cl.⁷ ................... C07D 501/36; C07D 501/34; C07F 7/18
(52) U.S. Cl. ................. 540/222; 540/225; 540/227; 540/228
(58) Field of Search ................. 540/222, 225, 540/227, 228

(56) References Cited

U.S. PATENT DOCUMENTS 4,458,072 A * 7/1984 Reiner et al. ............... 540/222

FOREIGN PATENT DOCUMENTS

| EP | 0 556 768 A | 8/1993 |
| EP | 0 791 596 A | 8/1997 |
| EP | 0 842 937 A2/A3 B1 | 5/1998 |
| PL | 163399 | 3/1994 |

OTHER PUBLICATIONS

Houben–Weyl, Methods of Organic Chemisrty, Additional and Supplementary Volumes to the 4th edition, vol. E221, "Synthesis of Peptides and Peptidomimetics", Georg Thieme Verlag 2002, p 443–445.
C. Morris, Ed, Academic Press Dictionary of Science and Technology, Academic Press Inc, 1992, headword "mixed anhydride", p. 1394.
Walter et al., "N–(Trimethylsilyl)thioharnstoffe," Liebigs Annalen der Chemie., No. 2, pp. 263–277 (1979), XP002142189, Verlag Chemie Gmbh. Weinheim, DE.
Gruber et al., "Eine neue Bildungsweise der Phosphor–Phosphor–Bindung," Chemische Berichte–Inorganic and Organometallic Chemistry—A European Journal., vol. 123(6), pp. 1313–1317 (1990) XP002142190, VCH Verlagsgesellschaft Mbh, Weinheim., DE.
Chemical Abstracts, 123:55587, Winiarski J. et al., "Method of preparing ceftriaxone", PL 163399 (Mar. 31, 1994).

* cited by examiner

*Primary Examiner*—Mark L Berch
(74) *Attorney, Agent, or Firm*—Hesna J. Pfeiffer

(57) ABSTRACT

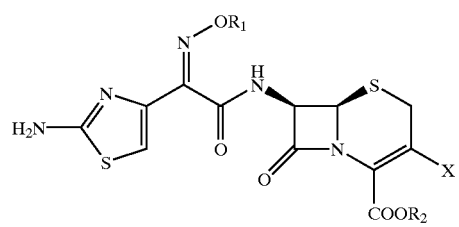

The present invention provides processes for the production of a compound of formula I wherein X, R1 and R2 are substituents conventional in cephalosporin chemistry; especially a compound of formula I is ceftrixone, cefotaxime; e.g., in the form of a salt.

7 Claims, No Drawings

β-LACTAM PRODUCTION

This is a continuation of International Application No. PCT/EP00/03428, filed Apr. 14, 2000, the contents of which are incorporated herein by reference.

The present invention relates to the production of β-lactams, such as pharmaceutically active β-lactams, e.g. cephalosporins, such as ceftriaxone or similar compounds.

In one aspect the present invention provides a process for the production of a compound of formula

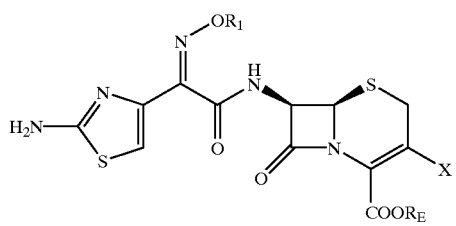

I wherein X and $R_1$ are substituents useful in cephalosporin chemistry and $R_E$ is hydrogen, a negative charge or together with the COO— group to which $R_E$ is attached is an ester, e.g. ceftriaxone or cefotaxime; comprising i) reacting a compound of formula

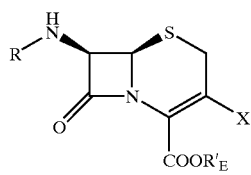

IV wherein R is hydrogen or silyl, $R'_E$ is silyl or together with the COO— group to which $R_E$ is attached is an ester; and X is as defined above, with a compound of formula

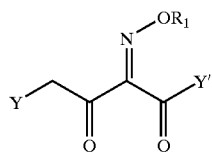

III wherein Y is halogen, Y' is a group which forms a basis that a compound of formula III is in a reactive form; and $R_1$ is as defined above, to obtain a compound of formula

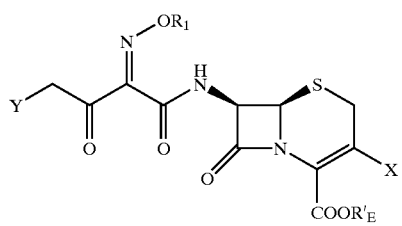

II wherein Y, X, $R'_E$ and $R_1$ are as defined above;

ii) reacting a compound of formula II wherein X, Y, $R'_E$ and $R_1$ are as defined above, with a compound of formula

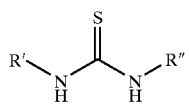

V wherein R' is hydrogen or silyl and R" is silyl; to obtain a compound of formula

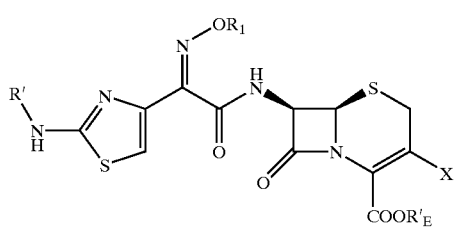

VI wherein X, $R_1$, R' and $R'_E$ are as defined above, and desilylating a compound of formula VI to obtain a compound of formula I; or ii') desilylating a compound of formula II wherein Y, X, $R'_E$ and $R_1$ are as defined above, and reacting a desilylated compound of formula II with thiourea in a solvent system containing organic solvent and water; e.g. and an alcohol; to obtain a compound of formula I;

e.g. a compound of formula I in free form; e.g. or a compound of formula I in the form of a solvate, or in the form of an ester or in the form of a salt, or in the form of an ester or in the form of a salt, and in the form of a solvate.

In another aspect the present invention provides a process for the production of a compound of formula I, wherein X, $R_1$ and $R_E$ are as defined above, e.g. ceftriaxone or cefotaxime; comprising reacting a compound of formula II, wherein Y, X, $R'_E$ and $R_1$ are as defined above, with a compound of formula V wherein R' and R" are as defined above according to step ii) as defined above; or desilylating a compound of formula II, wherein Y, X, $R'_E$ and $R_1$ are as defined above, and reacting a desilylated compound of formula II with thiourea according to step ii') as defined above, to obtain a compound of formula I;

e.g. a compound of formula I in free form; e.g. or a compound of formula I in the form of a solvate, or in the form of an ester or in the form of a salt; or in the form of an ester or in the form of a salt, and in the form of a solvate.

A compound of formula I in free form, in the form of an ester and in the form of a salt; e.g. and in the form of a solvate; e.g. or in the form of a non-solvate, may be obtained.

A compound of formula I in free form, e.g. and in the form of a solvate or in the form of a non-solvate; may be converted in the form of an ester or in the form of a salt; e.g. and in the form of a solvate, or in the form of a non-solvate; and vice versa. A compound of formula I in the form of a solvate may be converted into a compound of formula I in the form of a non-solvate and vice versa. Conversion may be carried out according to a method as conventional, e.g. including a method as conventional.

It is one advantage of the present invention that a compound of formula II needs not to be isolated in the course of the reaction. It is another advantage of the present invention that a process of the present invention may be a one-pot process.

In a compound of formula I,

X is a substituent useful in cephalosporin chemistry. A substituent useful in cephalosporin chemistry includes e.g. a substituent according to a substituent conventional in cephalosporin chemistry, e.g. including a substituent conventional in cephalosporin chemistry. A substituent useful in cephalosporin chemistry includes a substitutent which is useful in pharmaceutically active cephalosporins; and a substituent which is useful in intermediates for the production of pharmaceutically active cephalosporins. Preferably X is alkyl or alkenyl, more preferably methyl or ethenyl; e.g. including unsubstituted or substituted alkyl and alkenyl; e.g. unsubstituted alkyl and alkenyl, and alkyl and alkenyl substituted by alkoxy, heterocylcylthio, heterocycylcarbonylthio; alkylcarbonyloxy, preferably methylcarbonyloxy, heterocycly;

$R_1$ is a substituent useful in cephalosporin chemistry. Preferably $R_1$ is unsubstituted or substituted alkyl, e.g. unsubstituted alkyl, or alkyl substituted by carboxyl. More preferably $R_1$ is methyl; carboxymethyl; or a group of formula —C(CH$_3$)$_2$COOH.

$R_E$ is hydrogen, a negative charge or is, together with the COO— group to which $R_E$ is attached, an ester group; e.g. an ester group useful in cephalosporin chemistry.

If $R_E$ is a negative charge, the group X may contain a positive charge; e.g. in the form of a positively charged amine.

If $R_E$ together with the COO— group to which $R_E$ is attached is an ester group $R_E$ preferably forms with the COO— group a physiologically hydrolysable and acceptable ester, e.g. $R_E$ is a substituent useful in cephalosporin chemistry.

A compound of formula I may thus be in the form of a physiologically-hydrolysable and -acceptable ester. By physiologically-hydrolysable and -acceptable esters as used herein is meant an ester in which the COO— group together with $R_E$ forms an ester which is hydrolysable under physiological conditions to yield an acid which is itself physiologically tolerable at dosages to be administered. The term "$R_E$ together with the COO— group to which $R_E$ is attached is an ester group" is thus to be understood as defining regular pro-drug forms of a compound of formula I. A group —OR$_E$ may be preferably a group which is easily hydrolysable under physiological conditions. Such esters may be administered preferably orally, since hydrolysis usually takes place under the influence of the digestive enzymes. Parenteral administration may be indicated if the ester per se is an active compound or, if hydrolysis occurs in the blood.

If not otherwise defined herein heterocyclyl includes e.g. 5 or 6 membered heterocyclyl; e.g. including a bicyclic ring system, e.g. of 10 to 12 carbon atoms; e.g. hetrocyclyl having 1 to 4 heteroatoms; e.g. selected from N,O or S; e.g. including unsubstituted heterocyclyl or substituted heterocyclyl, e.g. unsubstituted heterocyclyl or heterocyclyl substituted; e.g. by one or more substituents; e.g. by a substituent useful in cephalosporin chemistry; e.g. heterocyclyl substituted by alkyl e.g. including (C$_{1-4}$)alkyl; carboxyalkyl; carbonyl. Alkyl includes (C$_{1-4}$)alkyl. Alkenyl includes (C$_{2-4}$)alkenyl. Alkoxy includes (C$_{1-4}$)alkoxy. Silyl includes trialkylsilyl, e.g. trimethylsilyl. Halogen (halo-) includes bromide, chloride, iodide.

A solvent system or solvent (system) includes one or more individual solvents.

Preferably a compound of formula I is cefdinir (see e.g. Merck Index, 12$^{th}$ edition, item 1971), cefditoren (see e.g. Merck Index, 12$^{th}$ edition, item 1972), cefepime (see e.g. Merck Index, 12$^{th}$ edition, item 1973), cefetamet (see e.g. Merck Index, 12$^{th}$ edition, item 1974), cefixime (see e.g. Merck Index, 12$^{th}$ edition, item 1975), cefmenoxime (see e.g. Merck Index, 12$^{th}$ edition, item 1976), cefodizime (see e.g. Merck Index, 12$^{th}$ edition, item 1979), cefotaxime (see e.g. Merck Index, 12$^{th}$ edition, item 1983), cefpirome (see e.g. Merck Index, 12$^{th}$ edition, item 1990), cefpodoxime and cefpodoxime proxetil (see e.g. Merck Index, 12$^{th}$ edition, item 1991), ceftazidime (see e.g. Merck Index, 12$^{th}$ edition, item 191995), cefteram (see e.g. Merck Index, 12$^{th}$ edition, item 1996), ceftiofur (see e.g. Merck Index, 12$^{th}$ edition, item 1999), ceftiaxone (see e.g. Merck Index, 12$^{th}$ edition, item 2001), cefuzonam (see e.g. Merck Index, 12$^{th}$ edition, item 2003); more preferably a compound of formula I is ceftriaxone or cefotaxim.

A compound of formula I includes a compound of formula I in free form, in the form of an ester and in the form of a salt; e.g. and in the form of a solvate or in the form of a non-solvate.

Step i) may e.g. be carried out as follows:

Compounds of formulae III and IV are known and may be prepared according to a method as conventional. In a compound of formula III, Y' is a group which forms a basis that a compound of formula III is in a reactive form; e.g. including halogen, a group which forms together with the —C=O group to which Y' is attached an active ester, and a group which forms together with the —C=O group to which Y' is attached a mixed anhydride.

If X and/or $R_1$ comprise silylatable groups (functions), such groups may be in silylated form in a compound of formulae II, IV and VI. If X and/or $R_1$ comprise silylated groups in a compound of formulae II or VI such groups are desilylated in step ii) or ii). Preferably a compound of formula II or of formula VI contains one or more silyl groups.

In another aspect the present invention provides a compound of formula II wherein R'$_E$, $R_1$ and Y are as defined above; e.g. a compound of formula II, wherein preferably R'$_E$ is silyl, $R_1$ is methyl and Y is defined as above; and X denotes a group of formula

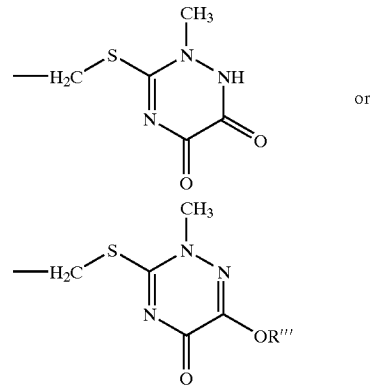

wherein R''' is silyl.

Such compounds are new, are e.g. useful intermediates, e.g. in the production of pharmaceutically active cephalosporins; e.g. and may be obtained by reaction of a compound of formula III, wherein Y is halogen, e.g. bromo, chloro; and Y' is halogen, e.g. chloro; with a compound of formula IV wherein R'$_E$ is silyl, and X is one of the above two mentioned groups; e.g. in an organic solvent (system).

Step ii) may be carried out as follows:

Thiourea may be silylated with a silylation agent in a solvent (system) inert under the reaction conditions. Appropriatesilylationagente.g.includessilylationagentsaccordingto conventional situation agents, e.g. including conventional silylation agents, e.g. mono- or bissilylated amides, e.g. derived from formamides, acetamides or trifluoroacetamides; bis-(trimethylsilyl)-urea or hexamethyidisilazane, e.g. in combination with an acid; halosilanes, e.g. chlorsilanes, e.g. in combination with an acid acceptor, e.g. an amine, such as triethylamine, tert.octylamine. A solvent (system) includes e.g. halogenated, e.g. chlorinated, hydrocarbons, such as dichloromethane; esters, e.g. ethyl acetate; and ethers; e.g. tetrahydrofuran. A compound of formula V, wherein R' and R" are as defined above, may be obtained.

In another aspect the present Invention provides a compound of formula V, wherein R' is hydrogen or tri($C_{1-4}$)alkylsilyl, e.g. trimethylsilyl; and R" is tri($C_{1-4}$)alkylsilyl; e.g. trimethylsilyl.

Compounds of formula V are useful intermediates, e.g. in the production of pharmaceutically active cephalosporins. If an equivalent amount or more of a silylation agent is used in respect with the two possible reaction sites in thiourea, a compound wherein both, R' and R", are tri($C_{1-4}$)alkylsilyl may be obtained. If an amount below the equivalent amount is used in respect with the two possible reaction sites in thiourea, e.g. an amount equivalent in respect with one of the possible reaction sites in thiourea, a compound of formula V may be obtained wherein R' is hydrogen and R" is tri($C_{1-4}$)alkylsilyl.

A compound of formula V may be obtained in the form of a mixture of a compound of formula V wherein R' is hydrogen and R" is tri($C_{1-4}$)alkylsilyl and a compound of formula V wherein both, R' and R", are tri($C_{1-4}$)alkylsilyl. A compound of formula V may be isolated, e.g. according to a method as conventional. In a reaction according to the present invention a compound of formula V is preferably not isolated.

E.g. according to step ii) a compound of formula II wherein $R'_E$, R., X and Y are as defined above; e.g. wherein In a group X and/or in a group $R_1$ silyl groups may be present; may be reacted with a compound of formula V, wherein R' and R" are as defined above, e.g. produced as described above or in the examples. That reaction may be carried out in a solvent (system), e.g. a solvent (system) as described above in the production of a compound of formula V. An add acceptor may be present, e.g. to bind an acid, e.g. formed in the course of the reaction; e.g. including mono- or bissilylated amides, e.g. as described above; or amines, e.g. trialkylamines, such as N,N-diisopropylethylamine.

A compound of formula VI wherein $R'_E$ is as defined above; e.g. wherein in a group X and/or $R_1$ silyl groups may be present; may be obtained.

In another aspect the present invention provides a compound of formula

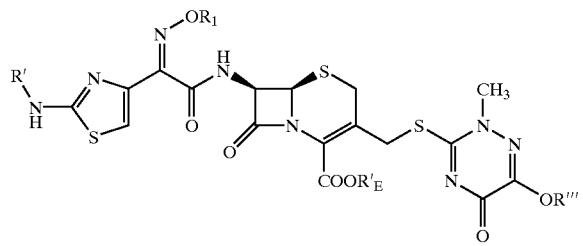

e.g. which is a compound of formula VI; wherein $R_1$ is as defined above, e.g. methyl; and R', $R'_E$ and R'" are tri($C_{1-4}$)alkylsilyl, e.g. trimethylsilyl; e.g. useful in the production of ceftriaxone, e.g. or similar compounds.

Desilylation of a compound of formula VI obtained in a process according to the present invention may be e.g. either carried out according to a method as conventional, e.g. by treatment with an alcohol and/or water and isolating a compound of formula I obtained; or may be carried out in the course of the isolation of a compound of formula I; e.g. a compound of formula I may directly be isolated from the reaction mixture containing a compound of formula VI comprising silyl groups, in free form, in the form of an ester or the form of a salt, and e.g. in the form of a solvate or in the form of a non-solvate; e.g. without isolating a compound of formula VI. This may be carried out e.g. according to a method as conventional; e.g. using appropriate extraction and isolation steps, such as:

E.g. Completing desilylation before isolating a compound of formula I;

e.g. Choosing optimal pH conditions in respect with stability and isolation of a compound of formula I, e.g. by use of buffer solutions, alkaline solutions or ammonium salt solutions of organic acids such as carbonates, carboxylates, phosphates, phosphonates and borates;

e.g. Choosing optimal conditions in respect with the solubility of a compound of formula I, e.g. Choosing optimal solvent (system) conditions; e.g. beside water, organic solvents may be used, e.g. alcohols, such as ($C_{1-4}$)-alcohols, such as 2-propanol; ketones, e.g. acetone; nitriles, e.g. acetonitrile; esters, e.g. methyl acetate; ethers, e.g. tetrahydrofuran; and amides, e.g. dimethylformamide;

e.g. Choosing an aqueous/organic solvent system which may optimize the separation of side products.

E.g. ceftriaxone in the form of a disodium salt; e.g. and in the form of a hemiheptahydrate, may be directly obtained from a reaction mixture containing a corresponding silylated ceftriaxone of formula VI, e.g. by treating the reaction mixture containing a silylated ceftriaxone, e.g. produced according to a process of the present invention, with a mixture of water and organic solvent which is miscible with water, e.g. acetone; and a base, e.g. a sodium source; e.g. sodium 2-ethylhexanoate; and with a mixture of water and an organic solvent which is able to from a two-phase system with water, e.g. dichloromethane. The pH of the mixture obtained is adjusted to about 6.5, e.g. 6.5; by addition of a base, e.g. sodium bicarbonate. A two-phase system is formed. The organic phase is separated off and the pH of the aqueous phase is adjusted to a pH of about 3, e.g. 3; by addition of an acid, e.g. hydrochloric add. A precipitate (ceftriaxone in free form) is obtained and filtrated off. The precipitate obtained is suspended in a mixture of water and organic solvent which is miscible with water, e.g. acetone; and the pH of the mixture obtained is is adjusted to about 6.5, e.g. 6.5; by addition of a sodium source, e.g. a sodium salt, e.g. sodium bicarbonate. A solution is obtained from which ceftriaxone in the form of a disodium salt; e.g. and in the form of a hemiheptahydrate; crystallizes and may be isolated, e.g. by filtration. E.g. by addition of further organic solvent, e.g. acetone; crystallization may be completed.

In another aspect the present invention provides a process for the production of ceftriaxone in the form of a disodium salt, e.g. and in the form of a hemiheptahydrate; e.g. in high purity; e.g. in crystalline form; comprising reacting a compound of formula II wherein Y is as defined above, $R_1$ is $CH_3$, $R'_E$ is silyl; and X is a group of formula

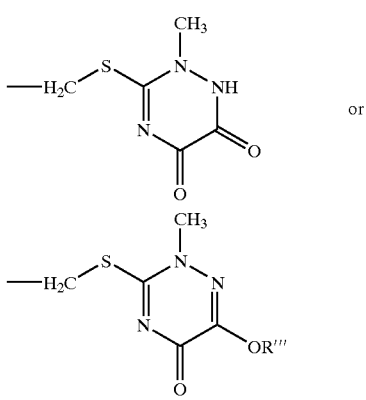

wherein R'" is as defined above, with a compound of formula V, wherein R' and R" are as defined above to obtain a compound of formula VI, wherein R'$_E$ is silyl; R$_1$ is CH$_3$, R' is as defined above and X is a group of formula

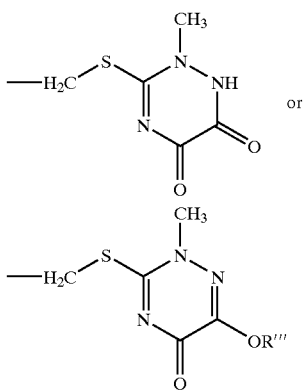

wherein R'" is as defined above; and
i) treating the reaction mixture obtained with water/organic solvent which is miscible with water, a base and with water/organic solvent which is able to form a two-phase system with water;
ii) adjusting the pH of the mixture obtained to about 6.5; e.g. by addition of a base;
iii) separating off the organic solvent from the two-phase system obtained;
iv) adjusting the pH of the aqueous phase obtained to a pH of about 3; e.g. by addition of an acid,
v) filtrating off the precipitate formed;
vi) suspending the precipitate obtained in a mixture of water and organic solvent which is miscible with water,
vii) adjusting the pH of the mixture obtained to about 6.5; e.g. by addition of a base; e.g. and adding acetone to the mixture obtained to complete crystallisation; and
viii) isolating ceftiaxone in the form of a disodium salt; e.g. and in the form of the hemiheptahydrate.

A process for the production of ceftriaxone in the form of a disodium salt according to the present invention may be e.g. carried out as follows:

A compound of formula II wherein R'$_E$, R$_1$, X and Y are as described above, e.g. obtained as described above; is desilylated, e.g. according to a method as conventional, e.g. by treatment with alcohol and/or water. A compound of formula II which is desilylated may be obtained and may be reacted, e.g. without isolation from the reaction mixture obtained; with thiourea in a solvent mixture (system) comprising water; e.g. in organic solvent, e.g. a solvent which is able to form a two-phase system with water, including halogenated, e.g. chlorinated hydrocarbons, e.g. dichloromethane, esters, e.g. acetic acid (C$_{1-4}$)alkyl esters; ethers, e.g. diisopropylethers; and in the presence of water; and e.g. in the presence of alcohols, such as an (C$_{1-4}$)alcohol, e.g. ethanol or isopropanol. Preferably an alcohol is present, e.g. in an appropriate amount e.g. including amounts of 5% to the double volume of the volume of the total solvent system used, e.g. in case of dichloromethane present as an organic solvent, including amounts of 5% to 30% of the volume of the total solvent system used. A base, e.g. an amine, e.g. triethylamine, may be present; e.g. in order to neutralize an halogenic acid set free in the course of the reaction. A compound of formula I may be obtained; e.g. in free form or in the form of a salt; and e.g. in the form of a solvate or in the form of a non-solvate; and may be isolated and e.g. may be purified; e.g. according to a method as conventional; e.g. or according to a method as described above.

In another aspect the present invention provides a process for the production of ceftriaxone in the form of a disodium salt, e.g. of formula

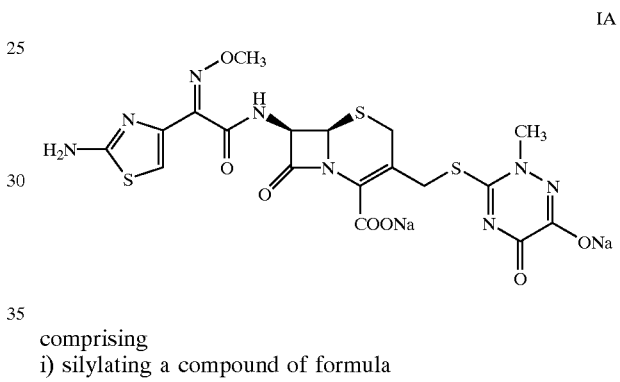

IA comprising
i) silylating a compound of formula

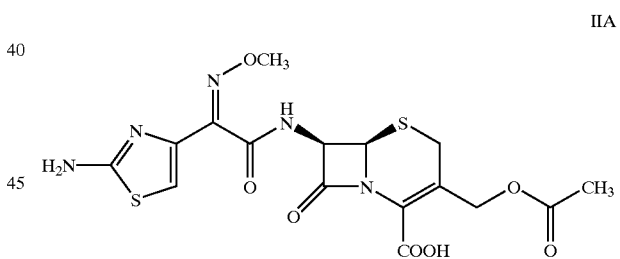

IIA or a compound of formula IIA in the form of a salt and iodinating; e.g. a compound obtained in silylation; to obtain a compound of formula

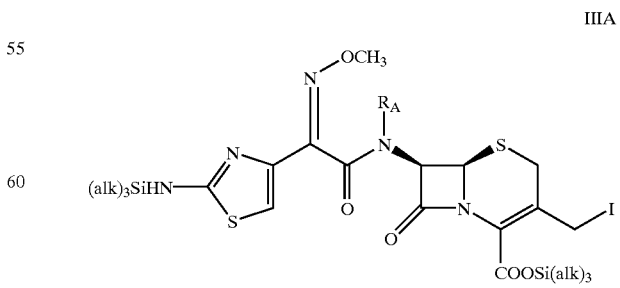

IIIA wherein R$_A$ is hydrogen or trialkylsilyl; e.g. trimethylsilyl; and alk is alkyl, e.g. methyl;

ii) reacting a compound of formula IIIA obtained in step i) with a compound of formula

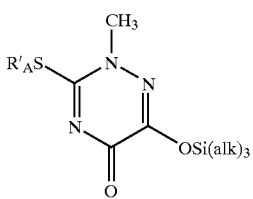

IVA wherein R'$_A$ is hydrogen or trialkylsilyl, e.g. trimethylsilyl; and desilylating; e.g. a compound obtained by reaction of a compound of formula IIIA with a compound of formula IVA;, to obtain a compound of formula

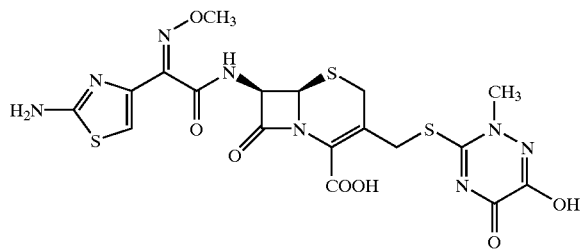

VA iii) isolating a compound of formula VA obtained in step ii) from the reaction mixture; and iv) converting a compound of formula VA obtained in step iii) into ceftriaxone in the form of a disodium salt; e.g. and in the form of a hemiheptahydrate.

A process for the production of a compound of formula VA according to the present invention may be carried out as follows:

Step i) may be carried out according to a method as conventional and is preferably carried out as follows:

In step i) a compound of formula IIIA may be obtained by treating a compound of formula IIA (e.g. the compound 7-[2-(aminothiazol-4-yl)-2(Z)(methoxylimino)acetamido]-3-(acetyloxy) methyl-3-cephem-4-carboxylic acid, i.e. cefotaxime in free form) or a compound of formula IIA in the form of a salt; e.g. in the form of an ammonium salt, or in the form of a sodium salt (sodium cefotaxime); preferably sodium cefotaxime; with a silylation agent and an iodination agent in a solvent (system).

Preferably sodium cefotaxime is used, e.g. in view of the fact, that cefotaxime in free form is a strongly solvating molecule, e.g. acetone and ethanol solvates of cefotaxime are known;

cefotaxime in free form may contain considerable amounts of water;

whereas sodium cefotaxim is poorly solvating and contains usually less amounts of solvent than cefotaxime in free form. Thus, if sodium cefotaxime is used instead of cefotaxime in free form, less silylation agent, e.g. trialkylsilylation; agent which may be reactive in respect with solvent (system), e.g. water and acetone, may be used.

Appropriate silylation agents include silylation agents usable according to conventional silylation processes; e.g. halosilanes, such as iodotrialkylsilane, e.g. iodotrimethylsilane (TMIS), e.g. in the presence of a nucleophile base; silylated amides, e.g. N,O-bis-(trimethylsilyl)-trifluoracetamide (BSTFA), N-methyl-N-trimethylsilyltrifluoracetamide (MSTFA); silazanes, e.g. 1,1,3,3,3-hexamethyidisilazane (HMDS); silylated ureas, such as bis-(trimethylsilyl)-urea (BSS), N,N'-bis-(trimethylsilyl)-urea (BSU); or a mixture of two or more of silylation agents; e.g.; a mixture of BSTFA or MSTFA or BSS or BSU with HMDS; preferably a mixture of BSTFA or MSTFA or BSS or HMDS with TMIS a mixture of BSTFA or MSTFA or BSS or HMDS with TMIS. The choice of a specific silylation agent may be important to enhance e.g. yield and purity of a desired compound of formula IIIA. if sodium cefotaxime is used for silylation preferably BSTFA, BSS or HMDS in combination with TMIS may be used. If cefotaxime in free form is used for silylation preferably HMDS, e.g. in the present of a silylation catalyst, e.g. including a silylation catalyst according to a conventional process; may be used. Preferably silylation is carried out before iodination.

An iodination agent includes an iodination agent usable in iodination reactions, e.g. according to a conventional iodination reaction, e.g. an iodination agent conventional in cepholosporin chemistry, e.g. an iodotrialkylsilane, preferably TMIS, e.g. produced in situ from iodine and hexamethlydisilane in dichloromethane. Preferably per mol of cefotaxime in free form or in the form of a salt 1.5 to 2.5 mol of iodination agent may be used. Iodination may be completed after silylation, e.g. a first amount of TMIS may be added to a compound of formula IIA preferably for silylation; and a second amount thereafter may be added for completing iodination.

To obtain a compound of formula IIIA wherein R'$_A$ denotes trialkylsilyl, e.g. after iodination, a corresponding higher amount of a silylation agent may be used than for the case where R'$_A$ denotes hydrogen.

An appropriate solvent (system) includes a solvent (system) inert under the reaction conditions, e.g. halogenated, e.g. chlorinated hydrocarbons, e.g. dichloromethane; nitriles; preferably dichloromethane.

A compound of formula IIIA obtained via silylation and iodination of a compound of formula IIA may be isolated, e.g. according to a process as conventional; but is preferably further reacted without isolation with a compound of formula IVA.

In step ii) a compound of formula IIIA; e.g. as obtained in step I); is reacted with a compound of formula IVA, e.g. silylated 3-mercapto-2-methyl(2,5-dihydro-6-hydroxy-5-oxo-as)-triazn; e.g. to obtain a compound of formula VA in a silylated form; and desilylating a compound of formula VA in a silylated form, to obtain a compound of formula VA; e.g. 7-[2-(aminothiazol-4-yl)2(Z)-(methoxyimino)acetamidol]-3-[(2,5-dihydro-6-hydroxy-2-methyl-5-oxo-as-triazin-3-yl) thio]-3-cephem-4-carboxylic add; in a solvent (system). Step ii) may be carried out according to a method as conventional and preferably may be effected as follows:

A compound of formula IVA which contains silylatable oxygen functions and which has a better solubility, e.g. in organic solvent (system); in a silylated form than in a non-silylated form, may be obtained by silylation of 3-mercapto-2-methyl-(2,5-dihydro-6-hydroxy-5-oxo-as)-triazin. Appropriate silylation agents include e.g. silylated amides; such as N,O-bis-(trimethylsilyl)-acetamide (BSA), N-methyl-N-trimethylsilyl-acetamide (MSA), BSS, BSU; or a silylation agent as appropriate in step i) for silylating a compound of formula IIA; of the present invention; preferably BSA. An appropriate solvent (system) includes solvent (system) inert under the reaction conditions, e.g. halogenated, e.g. chlorinated hydrocarbons, e.g. dichloromethane; nitriles, e.g. acetontrile; amides, e.g. dimethylacetamide; esters, e.g. ethylacetate; and ethers, e.g. tetrahydrofuran: preferably dichloromethane. BSA as a silylation agent together with dichloromethane as a solvent are preferred; e.g. in view of the finding of a quick silylation and easy solvent recovery.

Per mol of a compound of formula IIIA about 1 mol of a compound of formula IVA; e.g. or more; may be used. Preferably per mol of a compound of formula IIA, or of a compound of formula IIA in the form of a sodium salt 0.9 to 1.1 of a compound of formula VIA may be appropriate.

A compound of formula VA may be obtained which is isolated according to step iii) of the present invention.

Preferably steps i) and ii) may be carried out as follows:

Sodium cefotaxim in dichloromethane is silylated with a mixture of BSTFA or BSS with TMIS. 1.5 to 2.5 mol per mol of sodium cefotaxime are added to the reaction mixture obtained in silylation at appropriate temperatures, e.g.at a temperature from –20° to 20° C.; preferably from 0° bis 10°. A compound of formula IIIA is obtained and is reacted with a compound of formula IV, produced by reaction of 3-mercapto-2-methyl-(2,5-dihydro-6-hydroxy-5-oxo-as) triazin with BSA in dichloromethane. A compound of formula VA In a silylated form may be obtained.

Desilylation of a compound of formula VA in a silylated form may be carried out according to a method as conventional, e.g. by treatment with water and/or alcohol, e.g. in the presence of organic solvent (system); e.g. solvent originating from the reaction of a compound of formula IIIA with a compound of formula IVA; and e.g. in the presence of a base, preferably sodium acetate or an amine. More preferably a reaction mixture obtained in step ii) is mixed with an alcoholic solution of sodium acetate and water. A compound of formula VA may be obtained.

Step iii), i.e. isolation of a compound of formula VA, may be effected according to a method as conventional and is preferably effected as follows:

The pH of a reaction mixture obtained in step ii) may be adjusted to (about) 4 to 7, preferably to (about) 6 to 6.5, e.g. either after desilylation of a compound of formula VA in a silylated form; or during desilylation, e.g. in case that a base is used in the desilylation step; preferably after desilylation. A reducing agent may be added to the reaction mixture, e.g. in order to remove reduceable components present in the reaction mixture, e.g. iodine; e.g. including thiosulphate, bisulfite, ascorbinic add. Water and an organic solvent, which is able to form a A two-phase system with water, e.g. dichloromethane, is added to the mixture obtained and a two-phase system is formed. The phases are separated and the organic phase is dismissed. In order to remove colored impurities the aqueous phase may be treated with charcoal. After charcoal removal, the pH of the aqueous phase may be adjusted to (about) 2.0 to 3.5, e.g. 3.0. A compound of formula VA may precipitate and may be isolated, e.g. by filtration.

According to conventional methods in ceftriaxone production a compound of formula VA is usually not isolated from a reaction mixture containing it, but isolated in the form of a salt, e.g. directly as a compound of formula IA; or in the form of another salt, e.g. in the form of a dibenzylethylendiamine salt. We have found that isolation of a compound of formula VA according to the present invention surprisingly may improve the quality, e.g. purity, side product-profile (e.g. less side products), content, color; and may improve surprisingly the crystallisation behaviour; of a compound of formula IA, produced from an isolated compound of formula VA, e.g. compared with direct production of a compound of formula IA from a compound of formula VA without isolation of a compound of formula VA.

According to step iv) a compound of formula VA isolated in step iii) is converted into a compound of formula IA, e.g. ceftriaxone in the form of a disodium salt Step iv) may e.g. be carried out according to a conventional method and is preferably carried out as follows:

Preferably a compound of formula VA in isolated form, e.g. isolated as described in step iii), is further purified before conversion into a compound of formula IA. Further purification includes e.g. dissolution in an alcohol, e.g. methanol and charcoal treatment of the mixture obtained. For conversion a compound of formula VA is treated in a solvent (system) with a sodium source to obtain a pH of the mixture of (about) 5.0 to 7.0. A solvent (system) includes a mixture of organic solvent, preferably acetone; and water; e.g. in a range of organic solvent:water of e.g. 1:1 to 10:1; such as 3:1 to 8:1; e.g. 5:1. A sodium source includes e.g. a sodium salt, e.g. a sodium salt of an add, e.g. sodium hydroxide, carbonate, bicarbonate, acetate. Ceftriaxone in the form of a disodium salt, e.g. in the form of a hemiheptahydrate; may crystallize. Crystallization may be completed by addition of organic solvent, e.g. by addition of further acetone.

A compound of formula IA, i.e. ceftriaxone in the form of a disodium salt may be obtained and may be isolated in surprising high purity.

In another aspect the present invention provides a process for the production of a compound of formula

IB

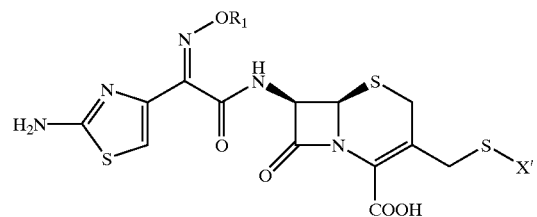

wherein X' and $R_1$ are substituents useful in cephalosporin chemistry; e.g. a compound of formula I is ceftriaxone; e.g. in free form, in the form of an ester or in the form of a salt; e.g. and in the form of a solvate; or in the form of a non-solvate; comprising i) silylating a compound of formula

IIB

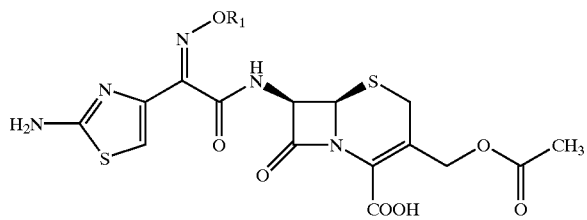

or a compound of formula IIB in the form of a salt, to obtain a compound of formula

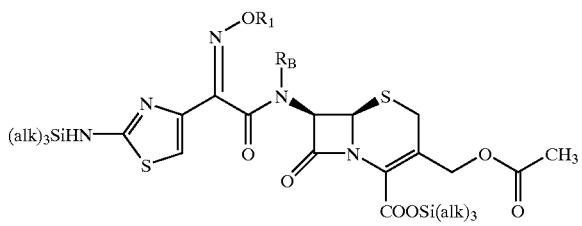

IIIB wherein $R_B$ is hydrogen or trialkylsilyl, and alk is alkyl;
ii) reacting a compound of formula IIIB with a compound of formula

  IVB wherein $R'_B$ is hydrogen or trialkylsilyl and X' is as defined above, in the presence of a compound of formula

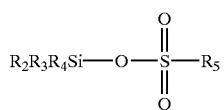  VB wherein $R_2$, $R_3$ and $R_4$ independently of each another are aryl or alkyl and $R_5$ is alkyl or aryl; e.g. trimethylsilyl-trifluoromethanesulfonate; and
iii) isolating a compound of formula IB from the reaction mixture obtained in step ii).

In a compound of formula IB, X' and $R_1$ are substituents useful in cephalosporin chemistry; e.g. $R_1$ is alkyl, e.g. methyl; and X' is heterocycly or heterocyclylcarbonyl, preferably heterocyclyl. A compound of formula IB is preferably ceftriaxone.

A compound of formula IIB is e.g. 7-[2-(aminothiazol-4-yl)-2(Z)-(methoxyimino)acetamido]-3-(acetyloxy)methyl-3-cephem-4-carboxylic acid (cefotaxime in free form). A compound of formula II may be in free form or in the form of a salt, e.g. an ammonium salt or a sodium salt, preferably in the form of a sodium salt (sodium cefotaxime).

In process step i) a compound of formula IIB is silylated with a silylation agent to obtain a compound of formula IIIB. Process step I) may e.g. be carried out according to a method as conventional. A preferred silylation agent includes e.g.
   if a compound of formula II is used (cefotaxime in free form) preferably HMDS, BSTFA, MSTFA, e.g. in any combination;
   if a compound of formula IIB is used in the form of the sodium salt (sodium cefotaxime) preferably BSS, BSTFA, HMDS, e.g. in in the presence of a halotrialkylsilane, such as trimethylchlorsilan (TMCS).

Appropriate solvent (system) in the production of a compound of formula IB in a silylated form according to the present invention include preferably solvent (system) which may advantageously be used in all reaction steps i) to ii); e.g. solvent (system) which is inert during the whole reaction sequence; e.g. and which is compatible under the reaction conditions. Appropriate solvent (system) includes halogenated, e.g. chlorinated hydrocarbons, e.g. dichloromethane, aliphatic and aromatic hydrocarbons, e.g. cyclohexane, toluene; nitriles, e.g. acetonitrile, e.g. including mixtures of individual solvents as mentioned above; preferably dichloromethane, cyclohexane; toluene.

A compound of formula IIIB may be obtained and may be isolated from the reaction mixture, e.g. according to a method as conventional; a compound of formula IIIB is preferably not isolated from the reaction mixture but further reacted in step ii).

Process step ii) may be carried out as follows:
A compound of formula IIIB is reacted with a compound of formula IVB in the presence of a compound of formula VB.

A compound of formula IVB may be obtained by silylation of a compound of formula IVB which is in a non-silylated form. Compounds of formula IVB and compounds of IVB in a non-silylated form are known or may be prepared e.g. according to a method as conventional. Silylation of a compound of formula IV in a non-silylated form may e.g. be carried out according to a method as conventional. The group X in a compound of formula IVB may comprise silylatable functions which are preferably silylated In the course of silylation of a compound of formula IVB. Preferred solvents include solvent as described in step i) above. Preferred silylation agents include e.g. HMDS, BSU, 2-trimethylsilyl-1-oxazolidinone (TMSO), TMCS, e.g. in the presence of a base; BSTFA, BSA; preferably BSTFA, which is highly reactive in the silylation of the thiol function and other silylatable functions, e.g. as present in a group X'.

Compounds of formula VB are known or may e.g. be prepared according to a method as conventional. The choice of a specific compound of formula VB may be dependent on the reactivity and availability of a compound of formula VB. E.g. trialkylsilyl-sulfonic acid esters; trimethylsilyl-trifluoromethanesulfonate (TMSTf), t-butyl-dimethylsilyl-trifluoromethansulfonate, trimethylsilyl-nonafluorobutanesulfonate, trimethylsilyl-methanesulfonate or trimethylsilyl-benzenesulfonate are commercially available.

Preferred compounds of formula VB include compounds of formula VB, wherein $R_2$, $R_3$ and $R_4$ independently of each another are aryl or alkyl, preferably alkyl; and $R_5$ is alkyl, preferably perfluorinated alkyl, e.g. —$CF_3$. Preferably $R_5$ is a strong electron withdrawing (electrophilic) substituent, e.g. perfluorinated alkyl; e.g. perfluorinated sulfonates; e.g. trifluorosulfonate; or aryl, carrying substituents which are strong electron withdrawing (electrophilic) substitutents; e.g. perfluorinated alkyl, perfluorinated sulfonates, e.g. methanesulfonates; nitro groups. A preferred compound of formula VB is trimethylsilyl-trifluoromethanesulfonate.

A compound of formula IIIB and a compound of formula IVB, e.g. commonly silylated in one pot; may be treated in a solvent (system); e.g. as described above; with a compound of formula VB; to obtain a compound of formula IB in a silylated form.

According to the present invention there are involved several silylation steps. In respect with silylation agents the following comments may be of interest:

The choice of the silylation agent may influence the reaction e.g. in view of the different silylated compounds which are used. E.g. a compound of formula VB is a strong silylation agent itsself and may thus silylate silylatable functions in molecules involved in the reaction sequence in the production of a compound of formula IB in a silylated form according to the present invention. In order to minimize the necessary amount of a compound of formula VB, it may be advantageous to achieve high silylation grades; i.e. silylation as complete as possible; in the production of a compound of formulae IIIB and IVB; although the reaction according to the present invention also works if compounds of formulae IIIB and IVB are incompletely silylated; e.g. if correspondingly the amount of a compound of formula VB is enhanced.

It is also advantageous to use such silylation agents in the silylation of a compound of formula IIIB and/or IVB, which; or which metabolites therof obtained after reaction; do not disturb the function of a compound of formula VB, e.g. by reaction with a compound of formula VB; e.g. which do not react with a compound of formula VB.

As already described above it should also be considered that the choice of a highly appropriate silylation agent may be dependent, whether a compound of formula IIB is used as such or in the form of a salt.

X' in a compound of formula IIB may further contain silylatable functions, which preferably should be already in a silylated form, e.g. as complete as possible, before a compound of formula VB is added to the reaction mixture.

The process of the present invention may be carried out e.g. in a one-pot reaction; e.g. a compound of formula IIB and a compound of formula IVB may be silylated commonly and may be reacted in the same pot with a compound of formula VB, e.g. to obtain a compound of formula IB in a silylated form.

Corresponding to the silylation grade achieved in a compound of formulae IIIB and IVB; including the silylation grade of a group X' comprising silylatable functions in a compound of formula IIIB; the necessary amount of a compound of formula VB may be determined and may be added in step ii) of the process of the present invention.

Process step iii) may be carried out according to a method as conventional and is preferably carried out as follows:

The reaction mixture obtained after reaction of the compounds of formulae IIIB with IVB in the presence of a compound of formula VB; e.g. to obtain a compound of formula IB in a silylated form; is treated in aqueous or alcoholic solvent system, e.g. in the presence of an organic solvent, e.g. including neutralization of the reaction mixture with a base.

Preferably a desilylation step is carried out; e.g. according to a method as conventional in desilylation reactions. E.g. preferably a base is added, e.g. an alkali salt of a weak acid, e.g. sodium acetate; or an amine; to a reaction mixture obtained in step i). The base may be dissolved in an alcohol, e.g. methanol; e.g. comprising water. A precipitate comprising a compound of formula IB may be formed upon addition of the base.

E.g. a compound of formula IB may be directly isolated by isolation of the precipitate formed; or via extraction steps. For isolation via extraction steps water and an organic solvent which is able to form a two-phase system with water may be added to the mixture obtained by addition of a base to a reaction mixture obtained in step ii). A two-phase system may be obtained and the pH of the mixture obtained may be adjusted and a compound of formula IB may be extracted into the aqueous phase. The aqueous phase may be purified by charcoal treatment. The pH of the aqueous phase may be adjusted to an acidic pH, e.g. an pH from 2.0 to 3.5 and a compound of formula IB may precipitate and may be isolated according to a method as conventional.

A compound of formula IB may be isolated in free form, or in the form of a salt from the reaction mixture; e.g. and in the form of a solvate. A compound of formula IB in free form, optionally in the form of a solvate; may be converted in a compound of formula IB in the form of a salt; preferably in the form of a pharmaceutically acceptable salt; e.g. and in the form of a solvate. Precipitation of a compound of formula IB in free form may also be circumvented, if desired. E.g. if a compound of formula IB in the form of a salt, e.g. a sodium salt, is desired to be isolatedd, a salt forming agent, e.g. including a sodium salt forming agent, e.g. sodium bicarbonate; may be added to an aqueous solution containing a compound of formula IB in free form and a compound of formula IB in the form of a salt, e.g. and in the form of a solvate; may be isolated from the reaction mixture. Alternatively a compound of formula IB may be isolated from the reaction mixture and may be converted in the form of a salt after isolation.

In a preferred embodiment of the present invention X' in a compound of formula IB denotes a group of formula

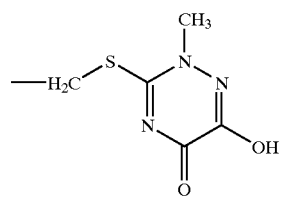

e.g. a compound of formula IB is ceftriaxone.

Ceftriaxone is preferably produced as follows:

A suspension of sodium cefotaxime in dichloromethane is cooled and silylated with BSS; e.g. 2 to 4 molequivalents BSS per mol of sodium cefotaxime (Solution A); e.g. to obtain a compound of formula III. A suspension of 3-mercapto-2-methyl-(2,5-dihydro-6-hydroxy-5-oxo-as)-triazin in dichloromethane is silylated with BSTFA, e.g. 1 to 5 molequivalents BSTFA per mol of sodium cefotaxime; to obtain a compound of formula VIIa or VIIb; or a mixture of a compounds of formula VIIa and VIIb:

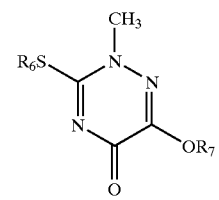

VIIa: $R_6$ = H, $R_7$ = Si(CH$_3$)$_3$
VIIb: $R_6$ $R_7$ = Si(CH$_3$)$_3$ (Solution B).

Solutions A and B are combined and 1 to 10 molequivalents of TMSTf are added per mol of sodium cefotaxime to the combined solutions.

Alernatively cefotaxime in free form and 3-mercapto-2-methyl(2,5-dihydro-6-hydroxy-5oxo-as)-triazin are commonly silylated in dichlormethane and TMSTf is added; e.g. 1 to 10 molequivalents TMSTf per mol of cefotaxime in free form; to the mixture obtained.

The reaction mixture obtained is combined with an aqueous and/or alcoholic mixture of water and sodium acetate or triethylamine. A precipitate may be formed and either the precipitate comprising ceftriaxone is filtrated off and ceftriaxone is isolated in the form of a precipitate; or a solvent which is able to form a two-phase system with water, e.g. dichloromethane; is added to the mixture obtained upon addition of an aqueous and/or alcoholic mixture of water and sodium acetate or triethylamine. A two-phase system is obtained and ceftriaxone is extracted into the aqueous phase, e.g. after pH adjustment to 5 to 7, preferably to 6 to 6.5 by addition of a base, e.g. a sodium salt of a weak acid, e,g, sodium bicarbonate or sodium acetate. The phases are separated and the aqueous phase is purified by charcoal treatment. E.g. in order to separate off water soluble contents from ceftriaxone, the pH of the aqueous phase may be adjusted to 1.0 to 3,5, e.g. 3.0. Ceftriaxone in free form may precipitate and may be filtrated off.

Ceftriaxone obtained may be further purified by dissolution in an alcohol, e.g. methanol or propylene glycol; and charcoal treatment. Low boiling alcohol, e.g. methanol may be evaporated off from the filtrate obtained after charcoal treatment The residue obtained, e.g. containing still alcohol, may be converted into ceftriaxone in the form of a disodium salt, e.g. by suspending ceftriaxone in free form in a mixture of acetone and water and adjusting the pH of the mixture obtained to 4 to 8, preferably to 5.8 in the presence of a sodium source; e.g. the sodium salt of a weak acid, e.g. sodium acetate or sodium bicarbonate. Crystalline ceftiaxone in the form of a disodium salt, e.g. in the form of a heptahydrate, may precipitate and may be isolated. Ceftriaxone in the form of a disodium salt may be obtained in high quality.

In the following examples all temperatures are given in degree Celsius.

The following abbreviations are used (herein and in the examples):

BSA: N,O-bis-(trimethylsilyl)-acetamide
BSS: bis-(trimethylsilyl)-sulfate
BSTFA: N,O-bis-(trimethylsilyl)trifluoracetamide
BSU: N,N'-bis(trimethylsilyl)urea
Cefotaxime in free form: 7-[2-(aminothiazol-4-yl)-2(Z)-(methoxyimino)acetamido]-3-(acetyl -oxy)methyl-3-cephem-4-carboxylic acid
Ceftriaxone in free form: 7-[2-(Aminothiazol-4-yl)-2(Z)-(methoxyimino)acetamido]-3-{[(2,5-di -hydro-6-hydroxy-2-methyl-5-oxo-as-triazin-3-yl)thio]methyl}-3-cephem -4-carboxylic acid
Disodium ceftriaxone; 7-[2(aminothiazol-4-yl)-2(Z)-(methoxyimino)acetamido]-3-{[(2,5-di -hydro-6-hydroxy-2-methyl-5-oxo-as-triazin-3-yl)thio]methyl}-3-cephem -4-carboxylic acid in the form of a disodium salt
HMDS: 1,1,1,3,3,3-hexamethyldisilazane
Sodium cefotaxime: 7-[2-(aminothiazol-4-yl)-2(Z)-(methoxyimino)acetamido]-3-(acetyl-oxy) methyl -3-cephem-4-carboxylic acid in the form of a sodium salt
TMIS: iodotrimethylsilane
TMSTf: trimethylsilyl-trifluormethansulfonate

EXAMPLE 1

7-[2-(Aminothiazol-4-yl)-2(Z)-methoxyimino)acetamido]-3-{[(2,5-dihydro-6-hydroxy-2-methyl-5-oxo-as-triazin-3-yl)thio]methyl}-3-cephem-4-carboxylic Acid in the Form of a Disodium Salt Solution A 18.57 g of 7-amino-3-{[(2,5-dihydro-6-hydroxy-2-methyl-5-oxo-as-triazin-3-yl)thio]methyl)}-3-cephem-4-carboxylic acid, suspended in 185 ml of dichloromethane, are treated under inert gas with 40.69 g of BSA while stirring the mixture at room temperature. The solution obtained is cooled to −10°.

Solution B 11.2 g of 4-bromo-2(Z)-methoximino-3-oxobutyric acid in 85 ml of dichloromethane, cooled to −10°, are treated under inert gas with 10.41 g of phosphorpentachloride, added in portions, while stirring.

Solution C 3.81 g of thio urea, suspended in 50 ml of dichloromethane, are treated under inert gas with 40.7 g of BSA while stirring. A clear solution is obtained.

Solution B is added to solution A while stirring at ca. −10° under an inert gas atmosphere, the mixture obtained is cooled to ca. 0° and treated with solution C under inert gas. The reaction mixture obtained is stirred at ca. 0° and poured while stirring onto an ice-cooled solution of 41.5 g of sodium 2-ethylhexanoate in 250 ml of acetone/water. The mixture obtained is stirred in an ice bath and 250 ml of water and 500 ml of dchloromethane are added. The pH of the two-phase system obtained is adjusted with sodium bicarbonate solution to 6.5. A two-phase system is obtained. The organic phase is separated off and the pH of the aqueous phase is adjusted to 3 with 2 N HCl. Precipitation occurs. The precipitate obtained is filtrated off and suspended in 250 ml of acetone and 15 ml of water. The pH of the suspension obtained is adjusted to 6.5 by addition of 1 M aqueous sodium acetate. A clear solution is obtained and crystallization occurs. Acetone is added while stirring. The precipitate obtained is filtrated off and dried. Ceftriaxone in the form of a disodium salt and in the form of a hemiheptahydrate is obtained.

EXAMPLE 2

7-[2-(Aminothiazol-4-yl)-2(Z)-methoximino)acetamido]-3-{[(2,5-dihydro-6-hydroxy-2-methyl-5-oxo-as-triazin-3-yl)thio]methyl}-3-cephem-4-carboxylic Acid in the Form of a Disodium Salt Solutions A and B are produced as described in Example 1, but using in solution B 8.98 g of 4-chloro-2(Z)-methoximino-3-oxo-butyric acid instead of 11.2 g 4-bromo-2(Z)-methoximino-3-oxo-butyric acid. Solutions A and B are mixed and poured onto a suspension of 21.0 g of sodium bicarbonate in 340 ml of wate/2-propanol while stirring. The pH of the two-phase system obtained is adjusted with 2 N HCl to 2.0. The organic phase is separated off and treated with 8.25 ml of water, 4.45 g of triethylamine and 3.35 g of thiourea while stirring. Precipitation occurs. The precipitate is isolated, suspended in 250 ml of acetone and 15 ml of water and treated with 1 M aqueous sodium acetate in water. A clear solution is obtained and crystallization occurs. Acetone is added under stirring to the mixture obtained. Ceftriaxone in the form of a disodium salt and in the form of a hemiheptahydrate is obtained.

EXAMPLE 3

7-[2-(Aminothiazol-4-yl)-2(Z)-methoximino)acetamido]-3-acetoxymethyl-3-cephem-4-carboxylic acid Solutions A and B are produced acording to a method as described in Example 2, but using in solution A 18.57 g of 7-aminocephalosporanic acid instead of 18.57 g of 7-amino-3-{[(2,5-dihydro-6-hydroxy-2-methyl-5-oxo-as-triazin-3-yl)thio]methyl}-3-cephem-4-carboxylic acid. While stirring the mixture obtained is poured onto an ice-cooled suspension of potassium bicarbonate in a mixture of water and 2-propanol. The pH of the two-phase system obtained is adjusted to 2.0 with 2 N HCl. The organic phase is separated off and treated with 7.5 ml of water and 3.81 g thiourea while stirring. The pH of the mixture is kept between 3.0 and 3.5 by addition of a solution of 2-amino-2,4,4-trimethylpentane in dichloromethane. A precipitate is obtained. 2-Propanol is added to the suspension obtained while stirring and the precipitate is isolated and dried.

7-[2-(Aminothiazol-4-yl)-2(Z)-methoximino)acetamido]-3-acetoxymethyl-3-cephem-4-carboxylic acid is obtained.

EXAMPLE 4

Ceftriaxone in Free Form

Solution A 23.87 g of sodium cefotaxim in 100 ml of dichloromethane are treated under inert gas with 19.31 g of BSTFA while stirring. To the mixture obtained 10.01 g of TMIS are added. The mixture obtained is cooled to 0° and treated with further 20.02 g of TMIS while stirring.

Solution B 7.95 g of 3mercapto-2-methyl-2,5-dihydro-6-hydroxy-5-oxo-as)-triazin in 32 ml of dichloromethane are treated with 11.19 g of BSA. A clear solution is obtained.

Solution B is added to Solution A and the mixture obtained is stirred under inert gas. The mixture obtained is poured onto a mixture of 20.5 g of sodium acetate in 350 ml of water/methanol, the mixture obtained is treated with 6.20 g of sodium thiosulphate pentahydrate and 250 ml of water and 500 ml of dichloromethane are added. The pH of the two-phase system obtained is adjusted to 6.5 with sodium bicarbonate. The organic phase is separated off and the aqueous phase is treated with charcoal. From the mixture obtained the charcoal is filtrated off and the pH of the filtrate obtained is adjusted to 3.0 with 2N HCl. Ceftriaxone in free form precipitates and is filtrated off.

EXAMPLES 5 and 6
Ceftriaxone in Free Form

Are carried out according to the method as described in example 4; but using a Solution A (Example 5) and a Solution A (Example 6) as described below instead of a Solution A as described in Example 4. Ceftriaxone in free form is obtained.

Solution A (Example 5)

23.87 g of sodium cefotaxime in 100 ml of dichloromethane are treated with 8.88 g of HMDS while stirring under inert gas. The mixture obtained is treated at ca. 0° with 11.01 g of TMIS, and with further 20.01 g of TMIS.

Solution A (Example 6)

22.77 g of cefotaxim in free form in 100 ml of dichloromethane are treated with 19.37 g of HMDS while stirring under inert gas. The mixture obtained is treated at ca. 0° with 20.01 g of TMIS and is further stirred.

EXAMPLE 7
Disodium Ceftriaxone

Ceftriaxone sodium obtained according to example 5 in 2500 ml of methanol is stirred with charcoal. The charcoal is filtrated off and solvent from the filtrate obtained is evaporated off at 30–35°. To the evaporation residue obtained 500 ml of acetone and 100 ml of water are added. The pH of the mixture obtained is adjusted to 5.8 with 5 M aqueous sodium acetate. Crystallisation occurs and is completed by addition of acetone. The precipitate obtained is filtrated off, washed with acetone and dried. Crystalline disodium ceftriaxone in the form of a hemiheptahydrate in a purity of 99.4% (HPLC, area) and a content of 83.7% is obtained.

REFERENCE EXAMPLE
Disodium Ceftriaxone Without Isolation of Ceftriaxone in Free Form Solution A and Solution B, produced according to Example 5, are reacted according to the description in Example 5 and worked up according to the description in Example 5; but omitting adjusting the pH of the aqueous solution obtained after filtrating off the charcoal and omitting isolation of ceftriaxone in free form according to Example 5. Instead, the aqueous solution obtained after filtrating off the charcoal according to the description in Example 5, is treated with 350 ml of acetone and the pH of the mixture obtained is adjusted to 5.8 with 5 M aqueous sodium acetate solution according to the description in example 7. The turbid solution obtained is seeded with disodium ceftriaxone obtained according to example 7. Crystallisation starts and is completed by addition of acetone according to the description 7. Crystalline dinatrium ceftriaxone is isolated and dried according to the description 7.

Crystalline disodium ceftriaxone in the form of a hemiheptahydrate in a purity of 98.1% (HPLC, area) and a content of 52.6% is obtained.

EXAMPLE 8
Disodium Ceftriaxone

Solution A 23.87 g of sodium cefotaxime in 100 ml of dichlormethane are treated with 30.31 g of BSS while stirring under inert gas in an ice-bath.

Solution B 7.95 g of 3-mercapto-2-methyl(2,5-dihydro-6-hydroxy-5-oxo-as)-triazine in 32 ml of dichloromethane are treated with 32.18 g of BSTFA while stirring and refluxing for several hours.

Solution B is added to solution A while stirring. The resulting mixture is treated under ice-cooling and inert gas with 38.90 g of TMSTf. The mixture obtained is poured into an ice-cooled solution of 20.5 g of sodium acetate in 350 ml of methanol/water and 250 ml of water and 500 ml of dichloromethane are added. The pH of the two-phase system obtained is adjusted with aqueous bicarbonate to 6.5. The organic phase is separated off and the aqueous phase is treated with charcoal. The charcoal is filtrated off and the pH of the filtrate obtained is adjusted to 3.0 with 2N HCl. A precipitate forms and the mixture is stirred in an ice-bath. The precipitate is filtrated off. The residue is dissolved in 3000 ml of methanol and treated with charcoal. The charcoal is filtrated off and solvent of the filtrate obtained is evaporated off at 30–35°. The evaporation residue obtained is treated with mit 300 ml of acetone and 150 ml of water adjusting the pH to ca. 5.8 with 5 M aqueous sodium acetate. To the mixture obtained 1500 of ml acetone are added and crystallisation occurs. The crystalline precipitate is filtrated off and dried.

Disodium ceftriaxone is obtained in a purity of 99.9% (HPLC, area).

EXAMPLE 9
Disodium Ceftriaxone—One Pot Procedure 23.87 g of cefotaxime in free form and 7.95 g of 3-mercapto-2-methyl-(2,5-dihydro-6-hydroxy-5-oxo-as)-triazin in 150 ml of dichloromethane are treated with 57.92 g of BSTFA while stirring under inert gas. A solution obtained is refluxed for several hours, cooled in an ice-bath, and treated with 33.34 g of TMSTf. The mixture obtained is poured onto an ice-cooled solution of 20.5 g of sodium acetate in 350 ml of methanol/water and 250 ml of water and 500 ml of dichloromethane are added. Further treatment and work-up is carried out according to the method described in example 8.

Disodium ceftriaxone is obtained in a purity of 99.6% (HPLC, area).

EXAMPLE 10
Disodium Ceftriaxone—One Pot Procedure 27.12 g of cefotaxime in free form and 8.12 g of 3-mercapto-2-methyl-(2,5-dihydro-6-hydroxy-5-oxo-as)-triazin in 100 ml of dichloromethane are refluxed under inert gas with 10.42 g of BSU. A precipitate obtained is filtrated off and the filtrate obtained is diluted with 100 ml of dichloromethane. 13.86 g of TMSTf are added to the mixture obtained under reflux. Under ice-cooling 5 g of ethanol and 7.5 g of triethylamine are added. A precipitate is obtained and is filtrated off. The solid residue is dissolved in 100 ml of propylene glycol, treated with charcoal and filtrated. The pH of the filtrate obtained is adjusted to 5.2 with 5 N aqueous sodium acetate. Crystallization occurs while adding acetone.

Disodium ceftriaxone is obtained as a fine, crystalline precipitate in a purity of 98.2% (HPLC, area).

What is claimed is:

1. A compound of formula

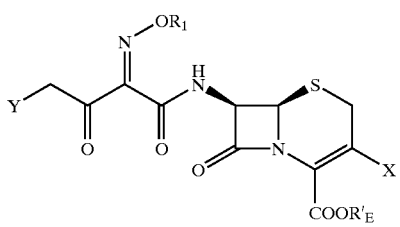

wherein $R'_E$ is trialkylsilyl or denotes with the coo— group to which $R'_E$ is attached an ester, $R_1$ is unsubstituted aklyl, or alkyl substituted by carboxyl, Y is halogen and X denotes a group formula

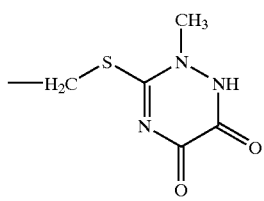

or

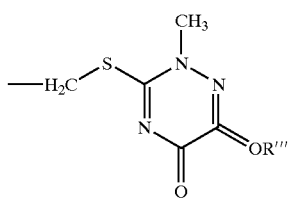

wherein R'" is trialkylsilyl.

2. A compound of formula

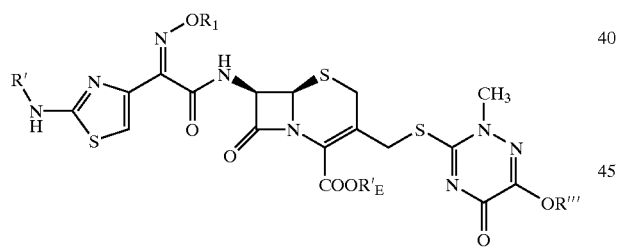

wherein $R_1$ is unsubstituted alkyl, or alkyl substituted by carboxyl, and R', $R'_E$ and R'" are tri($C_{1-4}$)alkyksilyl.

3. A process for the production of a compound of formula

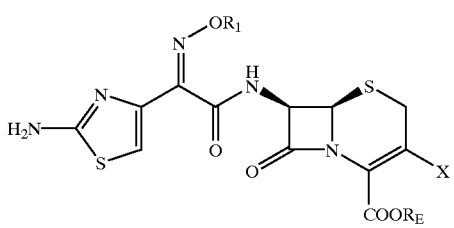

in free form, in the form of a solvate, in a salt form or in the form of a solvate of an ester or a salt,
wherein X is unsubstituted or substituted alkyl, or unsubstituted or substituted alkenyl, said substituted alkyl or alkenyl substituted by alkoxy, heterocyclythio, heterocyclylcarbonylthio, alkylcarbonyloxy or heterocyclyl, and $R_1$ is unsubstituted alkyl, or alkyl substituted by carboxyl, and $R_E$ is hydrogen or $R_E$ denotes together with the COO— group to which $R_E$ is attached an ester of a pharmaceutically acceptable salt, comprising either a) reacting a compound of formula

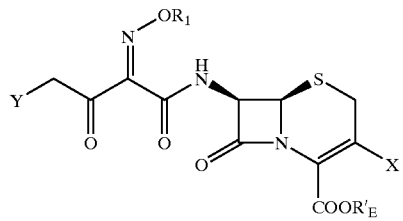

wherein Y is halogen, X and $R_1$ are as defined above and $R'_E$ is trialkylsilyl or denotes together with the COO— group to which $R'_E$ is attached an ester, with a compound of formula

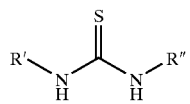

wherein R' is hydrogen or trialkylsilyl and R" is trialkylsilyl to obtain a compound of formula

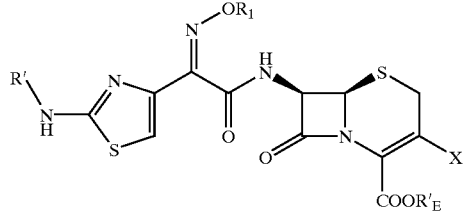

wherein X, $R_1$, R' and $R'_E$ are as defined above, and, optionally desilylating a compound of formula VI to obtain a compound of formula I; or a') desilylating a compound of formula II, wherein Y, X, and $R_1$ are as defined above and $R'_E$ is trialkylsilyl, and reacting a desilylated compound of formula II with thiorea in a solvent system containing organic solvent and water, to obtain a compound of formula I in free form, and thereafter optionally converting the compound of formula I to the salt form.

4. A process for the production of a compound of formula I according to claim 3 wherein the compound of formula II is prepared by reacting a compound of formula

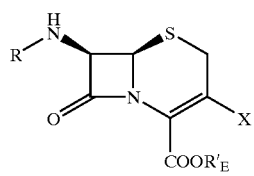

wherein R is hydrogen or trialkylsilyl or denotes together with COO— group to which R'$_E$ is attached to an ester; and X is as defined in claim 3, with a compound or formula

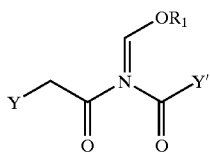   III wherein Y is halogen, Y' is halogen, or a group which forms together with the carbonyl- group to which Y' is attached an active ester or a mixed anhydride; and R$_1$ is as defined in claim 1, to obtain a compound of formula

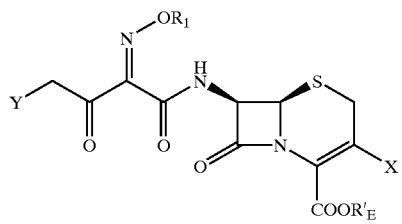   II wherein Y, X, R'$_E$ and R$_1$ are as defined in claim 3.

5. A process according to claim 3, wherein a compound of formula I is ceftriaxone or cefotaxime.

6. A process according to claim 3 wherein a compound of formula in the form of a solvate, or in the form of an ester or the form of a salt; or in the form of an ester or in the form of a salt, and in the form of a solvate.

7. A process for the production of ceftriaxone in the form of a disodium salt comprising reacting a compound of formula II

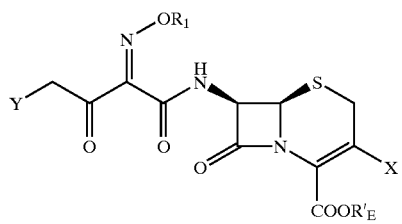   II wherein Y is halogen, R$_1$ is CH$_3$, R'$_E$ is trialkylsilyl, and X is a group of formula

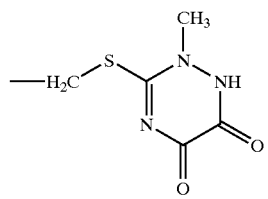

or

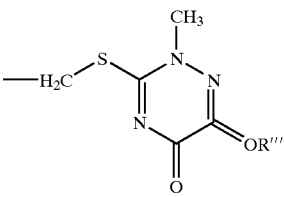

wherein R'" is trialkylsilyl, with a compound of formula V, wherein R' is hydrogen or trialkylsilyl and R'" is trialkylsilyl, to obtain a compound of formula VI, wherein R'$_E$ is trialkylsilyl; and R$_1$ is CH$_3$, is hydrogen or trialkylsilyl and X is a group of formula wherein R'" is as defined above; and i) reacting the reaction mixture obtained with water/organic solvent which is miscible with water and a base; and with water/organic solvent which is able to form a two-phase system with water;

ii) adjusting the pH of the mixture obtained to about 6.5;

iii) separating off the organic solvent from the two-phase system obtained;

iv) adjusting the pH of the aqueous phase obtained to a pH of about 3;

v) filtrating off the precipitate formed;

vi) suspending the precipitate obtained in a mixture of water and organic solvent which is miscible with water;

vii) adjusting the pH of the mixture obtained to about 6.5; and viii) isolating ceftriaxone in the form of a disodium salt.

* * * * *

UNITED STATES PATENT AND TRADEMARK OFFICE
CERTIFICATE OF CORRECTION

PATENT NO. : 6,552,186 B2
DATED : April 22, 2003
INVENTOR(S) : Gerlach et al.

It is certified that error appears in the above-identified patent and that said Letters Patent is hereby corrected as shown below:

Column 21,
Line 14, should read -- wherein $R'_E$ is trialkylsilyl or denotes together with the coo- group --.

Column 23,
Line 1, should read -- wherein R is hydrogen or trialkylsilyl $R'_E$ is trialkylsilyl or denotes together --.
Line 33, should read -- formula I is in the form of a solvate, or in the form of an ester --.
Line 34, should read -- or in the form of a salt; or in the form of an ester or in the form --.

Column 24,
Line 16, should read -- wherein R' is hydrogen or trialkysilyl and R" is trialkylsilyl, --.
Line 18, should read -- silyl; $R_1$ is $CH_3$, R' is hydrogen or trialkylsilyl and X is a --.

Signed and Sealed this

Fourth Day of November, 2003

JAMES E. ROGAN
*Director of the United States Patent and Trademark Office*